United States Patent
Vajda et al.

(10) Patent No.: US 10,501,410 B2
(45) Date of Patent: Dec. 10, 2019

(54) POCESS FOR THE PREPARATION OF HIGH PURITY PROSTAGLANDINS

(71) Applicant: CHINOIN GYÓGYSZER ÉS VEGYÉSZETI TERMÉKEK GYÁRA ZRT., Budapest (HU)

(72) Inventors: Ervin Vajda, Budapest (HU); Irén Hortobágyi, Budapest (HU); István Lászlofi, Budapest (HU); Péter Buzder-Lantos, Budapest (HU); Gábor Havasi, Budapest (HU); László Takács, Budapest (HU); Zsuzsanna Kardos, Budapest (HU)

(73) Assignee: CHINOIN GYÓGYSZER ÉS VEGYÉSZETI TERMÉKEK GYÁRA ZRT., Budapest (HU)

( * ) Notice: Subject to any disclaimer, the term of this patent is extended or adjusted under 35 U.S.C. 154(b) by 0 days.

(21) Appl. No.: 15/117,092

(22) PCT Filed: Mar. 11, 2015

(86) PCT No.: PCT/HU2015/000024
§ 371 (c)(1),
(2) Date: Aug. 5, 2016

(87) PCT Pub. No.: WO2015/136317
PCT Pub. Date: Sep. 17, 2015

(65) Prior Publication Data
US 2017/0037002 A1    Feb. 9, 2017

(30) Foreign Application Priority Data
Mar. 13, 2014 (HU) .................................... 1400140

(51) Int. Cl.
*C07C 405/00* (2006.01)
*B01D 15/32* (2006.01)

(52) U.S. Cl.
CPC .......... *C07C 405/00* (2013.01); *B01D 15/322* (2013.01)

(58) Field of Classification Search
None
See application file for complete search history.

(56) References Cited

U.S. PATENT DOCUMENTS

| | | | |
|---|---|---|---|
| 6,927,300 B2 | 8/2005 | Gutman et al. | |
| 7,498,458 B2 | 3/2009 | Greenwood et al. | |
| 2005/0209337 A1 | 9/2005 | Gutman et al. | |
| 2005/0261374 A1 | 11/2005 | Greenwood et al. | |
| 2008/0207926 A1 | 8/2008 | Martynow et al. | |
| 2010/0324313 A1 | 12/2010 | Hogan et al. | |

FOREIGN PATENT DOCUMENTS

| | | |
|---|---|---|
| EP | 2 208 724 A1 | 7/2010 |
| EP | 2 311 820 A1 | 4/2011 |
| WO | WO 01/055101 A2 | 8/2001 |
| WO | WO 02/096868 A2 | 12/2002 |
| WO | WO 02/096898 A2 | 12/2002 |
| WO | WO 2006/112742 A2 | 10/2006 |
| WO | WO 2010/104344 A2 | 9/2010 |
| WO | WO 2010/109476 A2 | 9/2010 |
| WO | WO 2011/005505 A2 | 1/2011 |
| WO | WO 2011/055377 A1 | 5/2011 |
| WO | WO 2011/095990 A2 | 8/2011 |
| WO | WO 213/133730 A1 | 9/2013 |

OTHER PUBLICATIONS

International Search Report (PCT/ISA/210) issued in PCT/HU2015/000024, dated Jun. 10, 2015.
Snyder et al., "Normal-Phase Chromatography", Introduction to Modern Liquid Chromatography, Third Edition, John Wiley & Sons, Inc., Jan. 14, 2010, XP055191770, pp. 361-402.
Wang et al., "Design and Synthesis of 13,14-Dihydro Prostaglandin $F_{1\alpha}$ Analogues as Potent and Selective Ligands for the Human FP Receptor", Journal of Medicinal Chemistry, American Chemical Society, vol. 43, No. 5, 2000, XP000929157, pp. 945-952.
Written Opinion (PCT/ISA/237) issued in PCT/HU2015/000024, dated Jun. 10, 2015.

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

The subject of the invention is a process for the preparation of high purity prostaglandin acid of the general formula II wherein the bonds marked with dotted lines represent single or double bonds wherein the double bonds may be cis- or trans oriented, Y represents O or $CH^2$, and $R^3$ stands for a phenyl group which is optionally substituted with $CF_3$, wherein the crude prostaglandin acid of the general formula II is purified by normal phase silicagel chromatography.

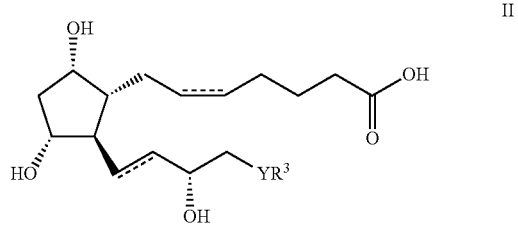

17 Claims, No Drawings

POCESS FOR THE PREPARATION OF HIGH PURITY PROSTAGLANDINS

The subject of the invention is process for the preparation of high purity prostaglandin derivatives of the general formula (I).

In the general formula (I)

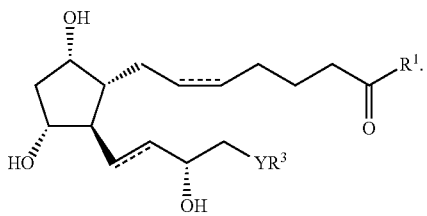

the bonds marked with the dotted lines represent single- or double bond where the double bond may be cis- or trans oriented, R$^1$ represents —OR$^2$ or —NR$^2$ group, wherein R$^2$ stands for straight or branched C$_{1-5}$ alkyl group or hydrogen atom Y represents oxygen atom or CH$_2$ group, and R$^3$ represents phenyl group, optionally substituted with —CF$_3$ group.

Significant representatives of the compounds of the general formula (I) are Latanoprost, Travoprost and Bimatoprost.

Latanoprost ((Z)-7-[(1R,2R,3R,5S)-3,5-Dihydroxy-2-[(3R)-3-hydroxy-5-phenylpentyl]-cyclopentyl]hept-5-enoic acid methylethyl ester) is a PGF$_{2\alpha}$ derivative used for the treatment of glaucoma (U.S. Pat. No. 5,242,368, British Journal of Ophthalmology, 1995, 79, 12-16).

Travoprost 7-[3,5-dihydroxy-2-[3-hydroxy-4-[3-(trifluoromethyl)phenoxy]-but-1-enyl]-cyclopentyl]hept-5-enoic acid isopropyl ester) is a known prostaglandin derivative used to treat glaucoma and high eye pressure (U.S. Pat. No. 5,510,383).

Bimatoprost (7-[(1R,2R,3R,5S)-3,5-dihydroxy-2-[(1E,3S)-3-hydroxy-5-phenyl-1-pentenyl]-cyclopentyl]-N-ethyl-5-heptenamide, (5Z)—) is a PGF$_{2\alpha}$ derivative used for the treatment of glaucoma (MedlinePlus, Jan. 1, 2003).

In the course of the known Latanoprost syntheses the main isomeric impurities arising from the synthesis are 15-epi-Latanoprost (15-(S)-Latanoprost) and 5,6-trans-Latanoprost. Physical and chemical characteristics of the isomeric impurities are very similar to those of Latanoprost, their removal is therefore a difficult task.

Preparation of high purity Latanoprost was first disclosed in the published patent application WO02/096898. Latanoprost was purified on normal phase preparative HPLC on silica gel column using isocratic eluent mixture. The eluent mixture contained one or more hydrocarbons (88-98%), one or more alcohols (2-18%) and optionally acetonitrile. Purity of the resulting Latanoprost ≥99.8%.

According to US20050209337A the Latanoprost acid ((Z)-7-[(1R,2R,3R,5S)-3,5-dihydroxy-2-[(3R)-3-hydroxy-5-phenylpentyl]cyclopentyl]hept-5-enoic acid) was purified by chromatography on silica gel column using dichloromethane:methanol eluent mixtures. The thus obtained acid had a purity of 98.4% with trans-isomer content of 1.3%. Latanoprost prepared from that acid was chromatographed first on silica gel column using heptane:isopropanol eluent mixtures, then by normal phase preparative HPLC using heptane:isopropanol=7:3 eluent mixtures. Purity: 99.9%.

In published patent application WO2006112742 Latanoprost acid was purified by "flash" chromatography on LiChroprep column using ethyl acetate-acetic acid eluent mixture, while Latanoprost prepared from the acid was purified by HPLC using hexane:isopropanol:acetic acid=91.5:8.40:0.10 or heptane:acetonitrile:isopropanol=94:2.5:3.5 eluent mixtures. Purity of the resulting Latanoprost ≥99.5%.

According to published European patent application No 2208724A high purity Latanoprost was obtained by purifying Latanoprost-prepared by known method—by gravimetric chromatography using methyl acetate, ethyl acetate, preferably isopropyl acetate as eluent, followed by purifying the obtained crude product by preparative HPLC (eluent: ethyl ether, propyl ether, preferably methyl tert.-butyl ether). The evaporated product was filtered on silica with heptane:isopropanol mixture, evaporated, dissolved in acetone and filtered on membrane filter. The process resulted high purity Latanoprost, the amount of the diastereomeric impurities was ≥0.1%.

Patent application US20100324313 discloses purification of prostaglandins on stationary phase (Chiralpak AD-H). The applied mobile phase contained supercritical carbon dioxide.

According to patent application WO2010104344 Latanoprost of ≥96% purity was obtained by chromatography of Latanoprost on silica gel with ethyl acetate:hexane=3:1 eluent mixture. This product was further purified by preparative HPLC using heptane:ethanol=94:6 eluent mixture to obtain high purity (≥99.8%) Latanoprost.

In patent application WO2010109476 Latanoprost is purified first by chromatography on silica gel column, then by preparative HPLC.

According to patent application WO2011055377 Latanoprost is purified by column chromatography, then by preparative HPLC. Purity of the obtained Latanoprost ≥99%.

Patent application WO2011095990 discloses purification of Latanoprost acid by reverse phase preparative HPLC. The eluent contains water and at least one organic solvent. The pH of the water is set to pH=2-5 with trifluoroacetic acid, the aqueous solution contains 0.01 mol of ammonium formate, ammonium acetate or D-tartaric acid.

As it is seen from the prior art, most of the known processes apply preparative HPLC method to obtain high purity Latanoprost. Disadvantage of the processes is that preparative HPLC technology is expensive, it requires costly investment and the method is not scalable.

According to the current quality requirements which have become into effect recently, the amount of the isomeric impurities may not exceed:

| Impurity | Previous requirement | Current requirement | USP |
| --- | --- | --- | --- |
| 15-epi-Latanoprost (15-(S)-Latanoprost) | ≤0.5% | ≤0.15% | ≤0.5% |
| 5,6-trans-Latanoprost | ≤3.5% | ≤0.15% | ≤3.5% |
| Non-identified impurities, induvidually | ≤0.1% | ≤0.10% | ≤0.1% |
| Non-identified impurities, total | ≤0.3% | — | ≤0.5% |
| Sum total of impurities | — | ≤0.50% | — |

Isomeric Impurities of Latanoprost Acid:

| Impurity | Previous requirement | Current requirement |
|---|---|---|
| 15-epi-Latanoprost acid (15-(S)-Latanoprost acid) | not given | ≤0.15% |
| 5,6-trans-Latanoprost acid | ≤4% | ≤0.15% |

Purity requirements for Travoprost and Bimatoprost are equally strict as well.

We aimed to elaborate a method for the purification prostaglandin derivatives where the strict requirements of high purity can be reached in an economical, industrial-scale process.

The phrase "high purity" means in this patent specification and claims that Latanoprost or Latanoprost acid of the formula (Ia) and (IIa) having high purity does not contain an individual isomeric impurity in amount of more than 0.15%. Travoprost and Travoprost acid of formula (Ib) and (IIb) having high purity does not contain trans-isomer impurity in amount of more than 1.45% and 15-epi-isomer in amount of more than 0.15%. Bimatoprost (Ic) having high purity does not contain trans-isomer impurity in amount of more than 0.50% and and 15-epi-isomer in amount of more than 0.50% and Bimatoprost acid of formula (IIc) having high purity does not contain trans-isomer impurity in amount of more than 0.75% and 15-epi-isomer in amount of more than 0.3%.

The non-identified impurities in Latanoprost (Ia), Travoprost (Ib) and Bimatoprost are individually not more than 0.10%.

Surprisingly we found that if we purify not the prostaglandin derivative of the general formula (I), but the appropriate acid of the general formula (II), where in the formula the dotted lines, Y and $R^3$ have the meanings as defined above, then, in simple and economical steps high purity prostaglandin derivatives can be obtained which meet even the strictest quality requirements.

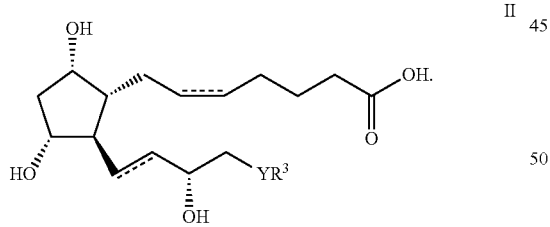

II

The basis of our invention is the finding that during the preparation of prostaglandin derivatives from the appropriate acids, no changes affecting the asymmetry centres or the structural isomerism take place, thus the high purity acid is suitable to prepare a high purity final product.

Our finding is all the more surprising, that according to the literature (U.S. Pat. No. 3,728,382) the separation of the prostaglandin acid isomers was carried out by transforming the acid into the methyl ester, separating the ester isomers and then saponifying them.

Details of our invention are demonstrated through purification of Latanoprost acid and Latanoprost.

According to our invention the crude Latanoprost acid is purified by chromatography and the resulting high purity Latanoprost acid is then esterified.

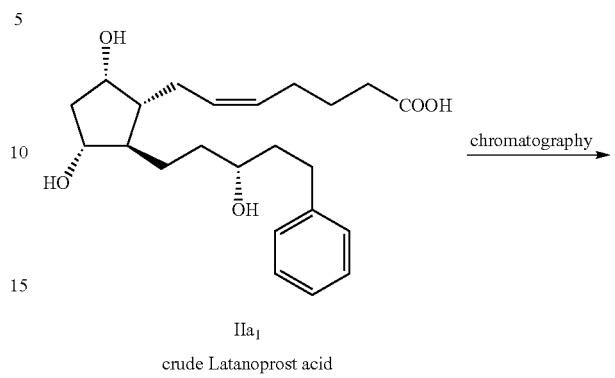

IIa$_1$ crude Latanoprost acid

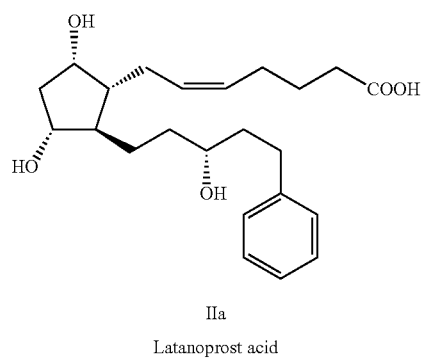

IIa

Latanoprost acid

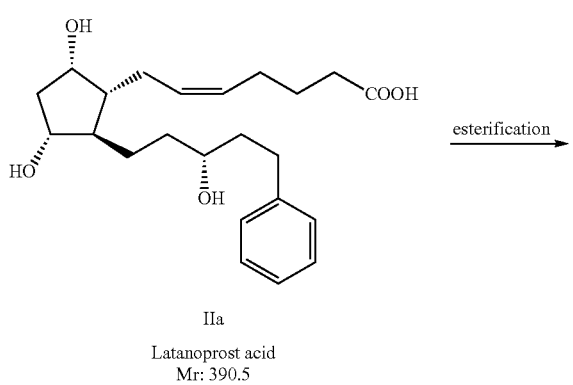

IIa

Latanoprost acid
Mr: 390.5

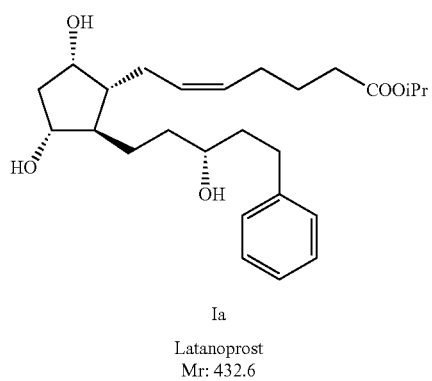

Ia

Latanoprost
Mr: 432.6

Impurities Arising from the Technology:

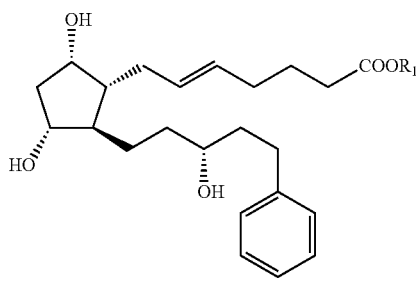

R$_1$ = H 5,6-trans-15-(R)-Latanoprost acid
R$_1$ = iPr 5,6-trans-15-(R)-Latanoprost
„trans-impurity"

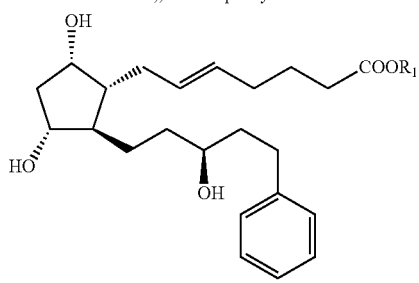

5,6-trans-15-(S)-Latanoprost acid
5,6-trans-15-(S)-Latanoprost
„15-epi-trans-impurity"

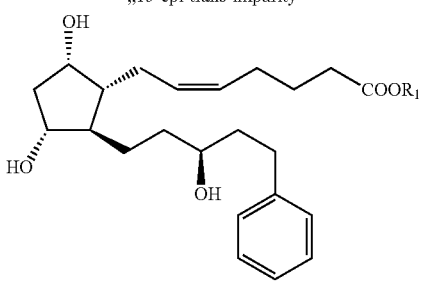

R$_1$ = H 5,6-cis-15-(S)-Latanoprost acid
R$_1$ = iPr 5,6-cis-15-(S)-Latanoprost
„15-epi-impurity"

According to our invention Latanoprost acid is purified by normal phase silica gel chromatography, preferably by normal phase gravitational, medium- or high pressure silica gel chromatography. The applicable pressure is in the range of below 20 bar in case of atmospheric or medium pressure chromatography and in a range of 20-40 bar in case of high pressure chromatography.

Irregular or spherical silica gels are applicable in a broad average particle size range of 5-200 micrometers. Different embodiments of our inventions include the use of spherical silica gels with average size of 10 or 15 or 20 or 50 or 75 or 150 micrometers.

The pore diameter of the applicable silica gels are generally below 300 angstrom and different embodiments of our invention include the use of silicagels having pore diameter in the range of 40-150 angstrom.

The applied eluent according to our invention is a multicomponent mixture which may contain one or more apolar, one or more polar solvent and solvent of acidic character in different ratios of the components One embodiment of our invention when the ratio of the apolar, polar and acidic character solvents is between (91-73%):(24-8.7%):(0.1-4.3%).

The apolar component of the mixture may be straight or branched open-chain, or cyclic, or aromatic hydrocarbon which may contain one or more substituents/halogen atom or other substituents. In some embodiments of our invention the applied apolar solvent is selected from aliphatic hydrocarbons as pentane, hexane, heptane, isooctane, or cyclohexane.

As polar solvent an alcohol-, ether-, ester- or ketone-type solvent or water may be applied which contain straight or branched open-chain or cyclic alkyl-, alkenyl- or cycloalkyl group. In some embodiments of the invention diethyl ether, diisopropyl ether, acetone, are used.

In some embodiments of the invention the applied polar solvent is a C$_{1-5}$ alcohol as among others methanol or ethanol or isopropyl alcohol.

The solvent of acidic character of the mixture may be an organic acid, optionally containing a halogen substituent.

In some embodiments of the invention the applied organic acid is a C$_{1-3}$ organic acid among others formic acid, acetic acid, monochlor-acetic acid or trifluoro-acetic acid.

In some embodiments of the invention the applied solvent system is hexane (91-73%) isopropanol (24-8.7%) acetic acid (0.1-4.3%) mixture.

After the chromatographical purification according to the invention, the amount of the isomeric impurities of Latanoprost acid is not more than 0.15%, individually.

Latanaprost is prepared by esterification of the high purity Latanoprost acid by known methods.

Purification of the crude Latanoprost obtained from the high purity Latanoprost acid IIa is carried out by chromatography.

The crude Latanoprost is subjected to normal phase silica gel chromatography, preferably to normal phase gravitational, medium- or high pressure silica gel chromatography. In several different embodiments of the crude Latanoprost chromatography irregular silica gels having 60-200 micrometer particle size or spherical silica gel 75 or 150 micrometer average particle size may be applied.

The applied eluent is a multicomponent eluent mixture which may contain one or more apolar and one or more polar solvents in a ratio of (65-31%):(9.1-2.4%).

The apolar solvent of the mixture may be straight or branched open-chain or cyclic or aromatic hydrocarbon which may contain one or more substituents among others selected from halogen atoms. In some embodiments of our invention the applied apolar solvent is a halogen containing open-chain hydrocarbon, such as dichloromethane, or an aliphatic hydrocarbon, such as pentane, hexane, heptane, octane, or cyclohexane.

As polar solvent an alcohol-, ether-, ester- or ketone-type solvent containing straight or branched open-chain or cyclic alkyl, alkenyl, or cycloalkyl group may be applied.

In an embodiment of our invention the applied polar solvent is a C$_{1-5}$ alcohol, among others methanol, isopropyl alcohol.

In an embodiment of our invention the applied eluent mixture is a gradient mixture made of hexane, dichloromethane and isopropanol and the composition of the mobile phase is periodically changed with the time.

Purity of the resulting Latanoprost is higher than 99.5%, the amount of the isomeric impurities is not more than 0.15%, individually.

The process according to the invention can also be applied for the purification of Travoprost acid of formula IIb and Bimatoprost acid of formula IIc.

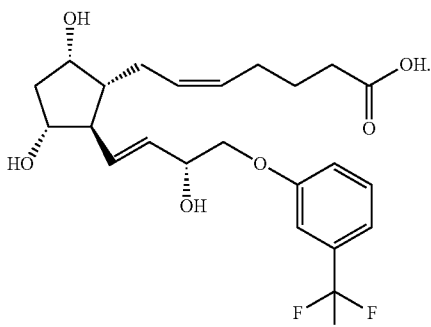

IIb

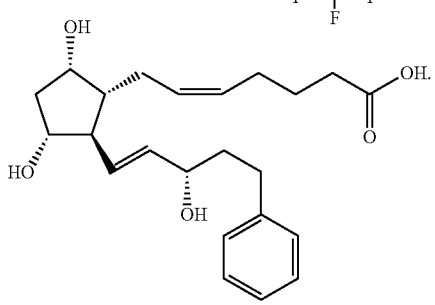

IIc

The applicable types of silicagels, compositions of eluent mixtures and applicable pressure ranges are the same in case of Travoprost acid and Bimatoprost acid as in case of Latanoprost acid.

Advantages of the purification process according to our invention, compared to the preparative and/or flash chromatographic methods comprise:
- the process is easily realizable in industry and the process saves costs,
- the highly effective purification is performed by gravitational chromatography, which is the most cost-saving chromatographic method, since:
- it does not require expensive pressure-proof equipments, in contrast to the medium- and high pressure chromatographic systems,
- the silica gel used for the stationary phase is cheaper than those used in the medium- and high pressure chromatographic systems, and finally
- on the gravitational column the purification is carried out in one run which shortens the production time.

One preferred embodiment of the process according to our invention is detailed below.

The crude Latanoprost acid of formula $IIa_1$ is synthesized a described in patent WO93/00329 by reacting the lactol of formula III with the phosphoran obtained from the triphenyl (carboxybutyl)phosphonium bromide of formula IV.

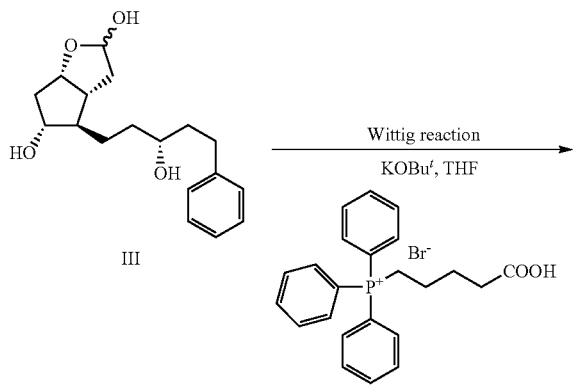

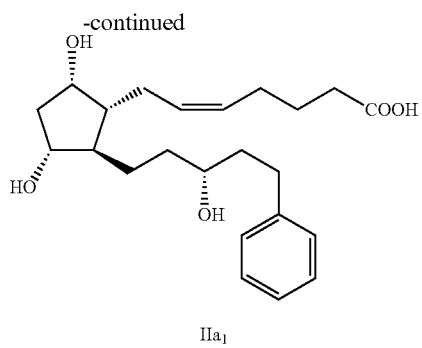

$IIa_1$

In the Wittig reaction, beside the desired cis isomer, Latanoprost acid of formula $IIa_1$, the trans isomer impurity is always formed, too.

Under the applied conditions the cis:trans ratio is 96:4 (amount of Latanoprost acid:amount of "trans-Latanoprost acid"=96:4). From the impurity which results the 15-epi Latanoprost acid, the "15-epi-trans-Latanoprost acid" is formed in the same ratio.

According to the targeted quality requirement the amount of the "15-epi-Latanoprost acid" may not be more than 0.15%, thus the amount of the "15-epi-trans-Latanoprost acid" will not be more than (0.15%*4%)/96% which equals 0.006%.

Therefore the amount of the "15-epi-trans-Latanoprost acid" is furthermore not evaluated.

The crude Latanoprost acid of formula $IIa_1$, obtained in known way, is purified before the esterification reaction.

Purification of the crude Latanoprost acid of formula $IIa_1$ is carried out by gravitational chromatography on a normal phase chromatography column filled with spherical silica gel.

As eluent hexane:isopropanol:acetic acid-10:1:0.11 mixture is used. Adequate fractions of the chromatography are united and evaporated.

In the evaporated main fraction of the chromatography:
- the amount of the "15-epi-Latanoprost acid" is ≤0.15 area %
- the amount of the "trans-Latanoprost acid" is ≤0.15 area %.

The evaporated main fraction which contains the purified Latanoprost acid (IIa) is esterified as described in patent application WO93/00329. Latanoprost acid (IIa) is then dissolved in dimethylformamide and reacted with isopropyl iodide in the presence of potassium carbonate. After completion of the reaction the mixture is worked up.

The evaporated Latanoprost crude product is purified by chromatography on silica gel column using gradient mixtures of hexane:dichloromethane:isopropanol as eluent. Adequate fractions of the chromatography are united and evaporated.

In the evaporated main fraction of the chromatography:
- the amount of the "15-epi-Latanoprost acid" is ≤0.15 area %
- the amount of the "trans-Latanoprost acid" is ≤0.15 area %
- unidentified impurities, individually are ≤0.10%
- sum total of impurities is ≤0.50%.

The evaporated main fraction is dissolved in isopropanol, filtered on membrane filter, evaporated and dried.

Further details of the invention are demonstrated by the following examples without limiting the invention to the examples.

EXAMPLES

Example 1a

Purification of Latanoprost Acid

(Z)-7-[(1R,2R,3R,5S)-3,5-Dihydroxy-2-[3(R)-3-hydroxy-5-phenylethyl]cyclopentyl]-5-heptenoic acid 165 g of crude Latanoprost acid IIa$_1$ is dissolved in dichloromethane. The solution is purified by gravitational chromatography on a column filled with spherical silica gel having 75 micrometer average particle size and 60 angstrom pore diameter/YMC GEL SIL S-75 type/using hexane:isopropanol:acetic acid=10:1:0.11 mixture as eluent. The fractions of sufficient purity are united and evaporated. Yield: 140 g (85%).

Starting Latanoprost Acid:

| | |
|---|---|
| Purity (HPLC area %) | 96.7% |
| trans-Latanoprost acid (HPLC area %) | 2.6% |
| 15-epi-Latanoprost acid (HPLC area %) | 0.14% |

Purified Latanoprost Acid:

| | |
|---|---|
| Purity (HPLC area %) | 99.4% |
| trans-Latanoprost acid (HPLC area %) | 0.02% |
| 15-epi-Latanoprost acid (HPLC area %) | 0.15% |

NMR Data:

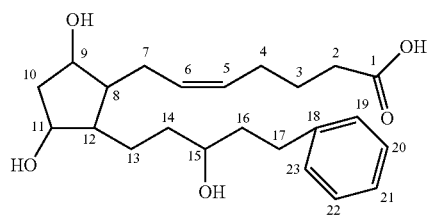

FIG. 1

TABLE 1

| Number | Function | Proton chemical shift/ppm | Proton spectrum integrated intensity | Carbon chemical shift/ppm |
|---|---|---|---|---|
| 1 | C | — | — | 174.9 |
| 2 | CH$_2$ | 2.19 | 2 | 33.7 |
| 3 | CH$_2$ | 1.54 | 2 | 25.1 |
| 4 | CH$_2$ | 2.03 | 2 | 26.6 |
| 5 | CH | 5.29 | 1 | 129.1 |
| 6 | CH | 5.46 | 1 | 130.4 |
| 7 | CH$_2$ | 2.15, 2.05 | 1, 1 | 26.4 |
| 8 | CH | 1.22 | 1 | 49.7 |
| 9 | CH(OH) | 3.88 (4.20) | 1(1) | 71.3 |
| 10 | CH$_2$ | 1.97, 1.47 | 1, 1 | 43.8 |
| 11 | CH(OH) | 3.62 (4.42) | 1(1) | 76.3 |
| 12 | CH | 1.50 | 1 | 50.9 |
| 13 | CH$_2$ | 1.39, 1.32 | 1, 1 | 28.9 |
| 14 | CH$_2$ | 1.41 | 2 | 35.3 |
| 15 | CH(OH) | 3.39 (4.38) | 1(1) | 69.9 |
| 16 | CH$_2$ | 1.62, 1.56 | 1, 1 | 39.6 |
| 17 | CH$_2$ | 2.69, 2.56 | 1, 1 | 32.0 |
| 18 | C | — | — | 143.1 |
| 19, 23 | CH | 7.18 | 2 | 128.7 |
| 20, 22 | CH | 7.25 | 2 | 128.7 |
| 21 | CH | 7.14 | 1 | 125.9 |

Example 1b

Purification of Latanoprost Acid

(Z)-7-[(1R,2R,3R,5S)-3,5-Dihydroxy-2-[3(R)-3-hydroxy-5-phenylethyl]cyclopentyl]-5-heptenoic acid 0.85 g of crude Latanoprost acid IIa$_1$ is dissolved in dichloromethane. The solution is purified by gravitational chromatography on a column filled with spherical silica gel having 150 micrometer average particle size and 60 angstrom pore diameter/YMC GEL SIL S-150 type/using hexane:isopropanol:acetic acid=10:1:0.11 mixture as eluent. The fractions of sufficient purity are united and evaporated. Yield: 0.697 g (82%).

Starting Latanoprost Acid:

| | |
|---|---|
| Purity (HPLC area %) | 96.7% |
| trans-Latanoprost acid (HPLC area %) | 2.6% |
| 15-epi-Latanoprost acid (HPLC area %) | 0.14% |

Purified Latanoprost Acid:

| | |
|---|---|
| Purity (HPLC area %) | 98.2% |
| trans-Latanoprost acid (HPLC area %) | 0.04% |
| 15-epi-Latanoprost acid (HPLC area %) | 0.14% |

Example 1c

Purification of Latanoprost Acid

(Z)-7-[(1R,2R,3R,5S)-3,5-Dihydroxy-2-[3(R)-3-hydroxy-5-phenylethyl]cyclopentyl]-5-heptenoic acid 0.85 g of crude Latanoprost acid IIa$_1$ is dissolved in dichloromethane. The solution is purified by gravity chromatography on a column filled with spherical silica gel having average particle size 40-75 micrometer and 70 angstrom pore diameter/Fuji Chromatorex MB70-40/75 type/using hexane:isopropanol:acetic acid=10:1:0.11 mixture as eluent. The fractions of sufficient purity are united and evaporated. Yield: 0.688 g (81%).

Starting Latanoprost Acid:

| | |
|---|---|
| Purity (HPLC area %) | 96.7% |
| trans-Latanoprost acid (HPLC area %) | 2.6% |
| 15-epi-Latanoprost acid (HPLC area %) | 0.14% |

Purified Latanoprost Acid:

| | |
|---|---|
| Purity (HPLC area %) | 99.4% |
| trans-Latanoprost acid (HPLC area %) | 0.16% |
| 15-epi-Latanoprost acid (HPLC area %) | 0.14% |

Example 1d

Purification of Latanoprost Acid (Z)-7-[(1R,2R,3R,5S)-3,5-Dihydroxy-2-[3(R)-3-hydroxy-5-phenylethyl]cyclopentyl]-5-heptenoic acid 1 gram of crude latanoprost acid $IIa_1$ is dissolved in dichloro-methane. The solution is purified by gravitational chromatography on a column filled with spherical silica gel having 75 micrometer average particle size and 60 angstrom pore diameter/YMC GEL SIL S-75 type/using different solvent mixtures as eluent listed in the below table. The fractions of sufficient purity are united and evaporated. The yields and the quality of the purified Latanoprost acid are listed in the Table 2:

bonate solution and water and then evaporated. The solid residue (crude Latanoprost) is dissolved in hexane:dichloromethane:isopropanol=20:10:1 mixture and purified by chromatography on irregular silica gel/average particle size: 63-200 micrometer, pore diameter: 60 angstrom/column using hexane:dichloromethane:isopropanol=20:10:1, hexane:dichloromethane:isopropanol=20:10:2 and finally hexane:dichloromethane:isopropanol=20:10:3 mixtures as eluents. For the dissolution and the chromatography distilled solvents are used.

The fractions of suitable purity are united and evaporated. The residue is dissolved in distilled isopropanol and filtered on membrane filter. The filtrate solution is evaporated and dried.

Yield: 105 g (68%) colourless oil.

| | |
|---|---|
| Assay (HPLC) | 99.8% |
| trans-Latanoprost (HPLC m %) | 0.04% |
| 15-epi-Latanoprost (HPLC m %) | 0.14% |

TABLE 2

| | | | | Quantity [g] | Purity HPLC area [%] | trans-Latanoprost acid HPLC area [%] | 15-epi-Latanoprost acid HPLC area [%] | Yield [%] |
|---|---|---|---|---|---|---|---|---|
| Starting Latanoprost acid | | | | 165 | 96.7 | 2.6 | 0.14 | — |
| Purified Latanoprost acid | | | | | | | | |
| 1 | Eluent: | Hexane:isopropanol:acetic acid | 10:1:0.11 | 140 | 99.4 | 0.02 | 0.15 | 85 |
| 2 | | Hexane:isopropanol:formic acid | 10:1:0.11 | 1.00 | 99.1 | 0.04 | 0.14 | 83 |
| 3 | | Hexane:isopropanol:trifluoro acetic acid | 10:1:0.10 | 1.00 | 89.9 | 0.05 | 0.15 | 82 |
| 4 | | Hexane:isopropanol:acetic acid | 9.5:1:0.11 | 1.00 | 99.3 | 0.03 | 0.14 | 76 |
| 5 | | Hexane:isopropanol:acetic acid | 10.5:1:0.11 | 1.00 | 99.5 | 0.04 | 0.14 | 79 |
| 6 | | Heptane:isopropanol:acetic acid | 10:1:0.11 | 1.00 | 99.2 | 0.06 | 0.15 | 79 |
| 7 | | c-Hexane:isopropanol:acetic acid | 9:1:0.11 | 1.00 | 99.3 | 0.06 | 0.13 | 68 |
| 8 | | c-Hexane:isopropanol:acetic acid | 10:1:0.11 | 1.00 | 99.0 | 0.03 | 0.14 | 76 |
| 9 | | c-Hexane:isopropanol:acetic acid | 15:1:0.11 | 1.00 | 99.3 | 0.02 | 0.13 | 80 |
| 10 | | Pentane:isopropanol:acetic acid | 10:1:0.11 | 1.00 | 99.1 | 0.04 | 0.14 | 67 |
| 11 | | Pentane:isopropanol:acetic acid | 15:1:0.11 | 1.00 | 99.2 | 0.03 | 0.13 | 80 |
| 12 | | isooctane:isopropanol:acetic acid | 10:1:0.11 | 1.00 | 99.1 | 0.05 | 0.15 | 78 |

Example 2

Preparation of Latanoprost (Ia)

5-Heptenoic acid, 7-[(1R,2R,3R,5S)-3,5-dihydroxy-2-[(3R)-3-hydroxy-5-phenylpentyl]cyclopentyl]-,1-methylethyl ester, (5Z)—

140 g of Latanoprost acid (IIa) is dissolved in dimethylformamide. To the solution 128.8 g of potassium carbonate and 80 ml of isopropyl iodide are added and the mixture is stirred at 50° C. After reaching the desired conversion, the reaction mixture is cooled and under agitation sodium hydrogen sulphate solution, hexane and ethyl acetate are poured to it. The phases are separated, the aqueous layer is extracted with hexane:ethyl acetate mixture. The organic phase is washed consecutively with sodium hydrogen car- NMR Data:

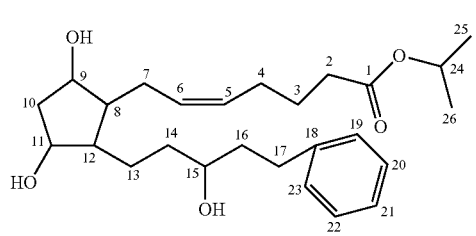

Figure 2

TABLE 3

| Number | Function | Proton chemical shift/ppm | Proton spectrum integrated intensity | Carbon chemical shift/ppm |
|---|---|---|---|---|
| 1 | C | — | — | 172.2 |
| 2 | $CH_2$ | 2.22 | 2 | 33.3 |
| 3 | $CH_2$ | 1.55 | 2 | 24.6 |
| 4 | $CH_2$ | 2.03 | 2 | 26.0 |
| 5 | CH | 5.29 | 1 | 128.4 |
| 6 | CH | 5.46 | 1 | 130.1 |
| 7 | $CH_2$ | 2.15; 2.04 | 1; 1 | 25.9 |
| 8 | CH | 1.21 | 1 | 49.2 |
| 19 | CH(OH) | 3.88 (4.19) | 1 (1) | 70.8 |
| 10 | $CH_2$ | 1.97; 1.47 | 1; 1 | 43.3 |
| 11 | CH(OH) | 3.62 (4.41) | 1 (1) | 75.9 |
| 12 | CH | 1.50 | 1 | 50.5 |
| 13 | $CH_2$ | 1.38, 1.32 | 1; 1 | 28.4 |
| 14 | $CH_2$ | 1.44; 1.40 | 1; 1 | 34.9 |
| 15 | CH(OH) | 3.38 (4.36) | 1 (1) | 69.5 |
| 16 | $CH_2$ | 1.63; 1.56 | 1; 1 | 39.1 |
| 17 | $CH_2$ | 2.69; 2.56 | 1; 1 | 31.5 |
| 18 | C | — | — | 142.6 |
| 19, 23 | CH | 7.18 | 2 | 128.2 |
| 20, 22 | CH | 7.26 | 2 | 128.2 |
| 21 | CH | 7.15 | 1 | 125.4 |
| 24 | CH | 4.86 | 1 | 66.8 |
| 25, 26 | $CH_3$ | 1.15 | 6 | 21.6 |

Example 3

Purification of Travoprost Acid

5-Heptenoic acid, 7-[(1R,2R,3R,5S)-3,5-dihydroxy-2-[(1E,3R)-3-hydroxy-4-[3-(trifluoromethyl)phenoxy]-1-buten-1-yl]cyclopentyl]-, (5Z)—

500 mg of Travoprost acid IIb is dissolved in dichloromethane. The solution is purified by gravity chromatography on a column filled with spherical silica gel having 75 micrometer average particle size and 60 angstrom pore diameter/YMC GEL SIL S-75 type/using hexane:isopropanol:acetic acid=10:1:0.11 mixture as eluent. The fractions of sufficient purity are united and evaporated. Yield: 420 mg (84%).

Starting Travoprost Acid:

| | |
|---|---|
| Purity (HPLC area %) | 97.34% |
| trans-Travoprost acid (HPLC area %) | 2.4% |
| 15-epi-Travoprost acid (HPLC area %) | 0.12% |

Purified Travoprost Acid:

| | |
|---|---|
| Purity (HPLC area %) | 98.26% |
| trans-Travoprost acid (HPLC area %) | 1.45% |
| 15-epi-Travoprost acid (HPLC area %) | 0.15% |

NMR Data:

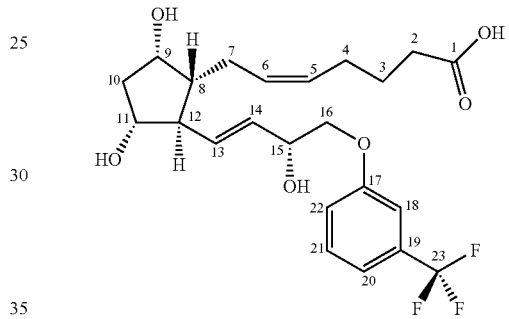

Figure 3

TABLE 4

| Number | $^{13}C/^{19}F$ (ppm) | $^1H$ (ppm) | Number of $^1H$ | Multiplicity | Coupling constant (Hz) (+/−0.2 Hz) |
|---|---|---|---|---|---|
| 1 | 174.37 | — | — | — | |
| 1-COOH | | 11.95 | 1 | broad (s) | |
| 2 | 33.09 | 2.13* | 2 | t | $J_{2,3}$ = 7.4 |
| 3 | 24.46 | 1.49** | 2 | m (tt) | $J_{3,4}$ = 7.4 |
| 4 | 26.06 | 1.96*** | 2 | m | |
| 5 | 128.56 | 5.23 | 1 | dt | $J_{5,6}$ = 10.7; $J_{4,5}$ = 7.2 |
| 6 | 129.73 | 5.43 | 1 | dt | $J_{6,7}$ = 7.4 |
| 7 | 24.78 | b:2.10* | 1 | m | |
| | | a: 1.96*** | 1 | m | |
| 8 | 48.78 | 1.32 | 1 | m (dddd/tt) | 11.1; 10.0; 5.0; 5.0 |
| 9 | 69.58 | 3.90+ | 1 | m | |
| 9-OH | | 4.36++,$ | 1 | broad (s) | |
| 10 | 43.96 | b: 2.20* | 1 | ddd | $J_{gem}$ = 14.1; $J_{10b,11}$ = 8.4; $J_{9,10b}$ = 5.8; $J_{10a,11}$ = 5.6; $J_{9,10a}$ = 2.3; |
| | | a: 1.44** | 1 | ddd | |
| 11 | 75.64 | 3.69 | 1 | m | |
| 11-OH | | 4.53 | 1 | broad (s) | |
| 12 | 54.30 | 2.18* | 1 | m (td) | |
| 13 | 133.97 | 5.57 | 1 | dd | $J_{13,14}$ = 15.5; $J_{12,13}$ = 8.0 |
| 14 | 131.01 | 5.51 | 1 | dd | $J_{14,15}$ = 5.7 |
| 15 | 69.51 | 4.32++ | 1 | q (ddd) | 5.6 |
| 15-OH | | 5.125$ | 1 | broad (s) | |

TABLE 4-continued

| Number | $^{13}C/^{19}F$ (ppm) | $^1H$ (ppm) | Number of $^1H$ | Multiplicity | Coupling constant (Hz) (+/−0.2 Hz) |
|---|---|---|---|---|---|
| 16 | 72.55 | b: 3.96+ | 1 | dd | $J_{gem}$ = 9.9; |
|  |  | a: 3.93+ | 1 | dd | $J_{15,16b}$ = 4.9 |
|  |  |  |  |  | $J_{15,16a}$ = 6.6 |
| 17 | 158.97 | — | — | — |  |
| 18 | 111.13 (q) | 7.20+ | 1 | m (t/dd) | $^3J_{C-18,F}$ = 3.7 |
|  |  |  |  |  | $J_{18,20}$ = 1.5; |
|  |  |  |  |  | $J_{18,22}$ = 2.5 |
| 19 | 130.29 (q) | — | — | — | $^2J_{C-19,F}$ = 31.7 |
| 20 | 117.01 (q) | 7.26+++ | 1 | m (ddd) | $^3J_{C-20,F}$ = 3.8; |
|  |  |  |  |  | $J_{20,21}$ = 7.8; |
|  |  |  |  |  | $J_{20,22}$ = 0.7 |
| 21 | 130.68 | 7.50 | 1 | t (dd) | $J_{21,22}$ = 8.2 |
| 22 | 118.75 | 7.24+++ | 1 | m (ddd) |  |
| 23 | 124.01 (q) | — | — | — | $^1J_{C-23,F}$ = 272.4 |
| 23-F | −61.19 (s, 3) | — | — | — |  |

*,,*,+,++,+++Overlapping $^1H$ NMR signals
$these coupling constants and chemical shifts are determined on the basis of the literature data of Travoprost

Example 4

Purification of Bimatoprost Acid

5-Heptenoic acid, 7-[(1R, 2R, 3R, 5S)-3,5-dihydroxy-2-[(1E,3S)-3-hydroxy-5-phenyl-1-penten-1-yl]cyclopentyl]-, (5Z)—

500 mg of Bimatoprost acid lie is dissolved in dichloromethane. The solution is purified by gravity chromatography on a column filled with irregular silica gel having 50 micrometer average particle size and 65 angstrom pore diameter/Sepra Silica 50 type/using diisopropyl ether:acetone:water=40:25:1 mixture as eluent. The fractions of appropriate purity are united and evaporated. Yield: 210 mg (42%).

Starting Bimatoprost Acid:

| Purity (HPLC area %) | 95.09% |
|---|---|
| trans-Bimatoprost acid (HPLC area %) | 1.51% |
| 15-epi-Bimatoprost acid (HPLC area %) | 0.08% |

Purified Bimatoprost Acid:

| Purity (HPLC area %) | 98.95% |
|---|---|
| trans-Bimatoprost acid (HPLC area %) | 0.75% |
| 15-epi-Bimatoprost acid (HPLC area %) | 0.3% |

NMR Data:

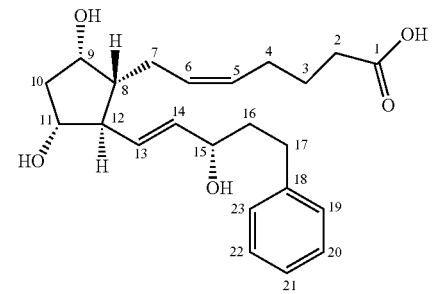

Figure 4

TABLE 5

| Number | $^{13}C$ (ppm) | $^1H$ (ppm) | Number of $^1H$ | Multiplicity | Coupling constant (Hz) (+/−0.2 Hz) |
|---|---|---|---|---|---|
| 1 | 174.34 | — | — | — |  |
| 1-COOH |  | 11.96 | 1 | broad |  |
| 2 | 33.15 | 2.12* | 2 | m (t) | $J_{2,3}$ = 7.4 |
| 3 | 24.51 | 1.49** | 2 | m (tt) | $J_{3,4}$ = 7.2 |
| 4 | 26.14 | 1.975*** | 2 | m (q) | $J_{4,5}$ = 7.2 |
| 5 | 128.58 | 5.26 | 1 | dt | $J_{5,6}$ = 10.7 |
| 6 | 129.69 | 5.455+ | 1 | m (dt) | $J_{6,7}$ = 7.7 |
| 7 | 24.79 | 2.11* | 1 | m |  |
|  |  | 1.995*** | 1 | m |  |
| 8 | 48.86 | 1.30 | 1 | m (dddd) | 10.5; 10.5; 5.2; 5.2 |
| 9 | 69.51 | 3.91++ | 1 | m |  |
| 9-OH |  | 4.35 | 1 | broad |  |
| 10 | 43.95 | β: 2.19* | 1 | m(ddd) | $J_{gem}$ = 14.1; |
|  |  | α: 1.44** | 1 | m (ddd) | 8.3; 6.0 |
|  |  |  |  |  | 5.6; 2.2 |
| 11 | 75.74 | 3.67 | 1 | m (td/dddd) | 7.5; 7.5; 6.4 |
| 11-OH |  | 4.50 | 1 | broad |  |
| 12 | 54.26 | 2.15* | 1 | m |  |

TABLE 5-continued

| Number | $^{13}$C (ppm) | $^1$H (ppm) | Number of $^1$H | Multiplicity | Coupling constant (Hz) (+/−0.2 Hz) |
|---|---|---|---|---|---|
| 13 | 132.08 | 5.365 | 1 | dd | $J_{13,14}$ = 15.4; $J_{12,13}$ = 8.2 |
| 14 | 135.15 | 5.43$^+$ | 1 | m (dd) | $J_{14,15}$ = 6.3 |
| 15 | 70.57 | 3.90$^{++}$ | 1 | m | |
| 15-OH | | 4.66 | 1 | broad | |
| 16 | 39.52$^\$$ | 1.71$^{+++}$ | 1 | m | |
| | | 1.65$^{+++}$ | 1 | m | |
| 17 | 31.34 | 2.58$^\#$ | 1 | m | |
| | | 2.615$^\#$ | 1 | m | |
| 18 | 142.29 | — | — | — | |
| 19, 23 | 128.20 | 7.17$^{\#\#}$ | 2 | d | $J_{19,20}$ = 7.4 |
| 20, 22 | 128.24 | 7.26 | 2 | t | $J_{20,21}$ = 7.4 |
| 21 | 125.55 | 7.15$^{\#\#}$ | 1 | t | |

$^\$$$^{13}$C NMR signals are overlapping with the signals of DMSO.

*,,*,+,++,+++,#,##Overlapping $^1$H NMR signals.

The invention claimed is:

1. A process for the purification of latanoprost acid of Formula IIa:

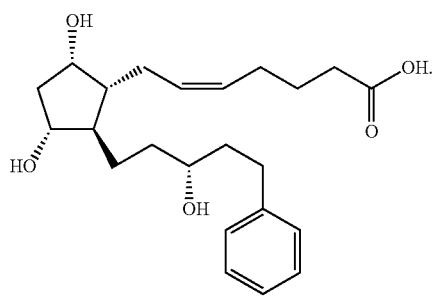

which consists of purifying crude latanoprost acid of Formula IIa by gravitational chromatography on a normal phase chromatography column filled with silica gel so that the purified latanoprost acid of Formula IIa has a purity of 89.9%-99.5% and isomeric impurities of trans-latanoprost acid and 15-epi-latanoprost acid obtained in the process are not individually more than 0.15%,
wherein a multicomponent eluent mixture is applied as eluent, and
wherein the eluent mixture contains one or more apolar solvents, one or more polar solvents and solvent of acidic character, in a ratio of (91-73%):(24-8.7%):(0.1-4.3%).

2. The process as defined in claim 1, wherein the applied silica gel is a spherical silica gel having average particle size in a range of 75-150 micrometer.

3. The process as defined in claim 1, wherein the apolar component of the eluent mixture is straight or branched open-chain or cyclic or aromatic hydrocarbon, optionally containing one or more substituents.

4. The process as defined in claim 3, wherein the substituent is halogen atom.

5. The process as defined in claim 3, wherein as apolar solvent aliphatic hydrocarbon is applied.

6. The process as defined in claim 1, wherein as polar solvent an alcohol-, ether-, ester- or ketone-type solvent is applied which contains straight or branched open-chain alkyl, alkenyl or cyclic or cycloalkyl group.

7. The process as defined in claim 6, wherein as polar solvent $C_{1-5}$ alcohol is applied.

8. The process as defined in claim 7, wherein as polar solvent isopropyl alcohol is applied.

9. The process as defined in claim 1, wherein the solvent of acidic character of the solvent mixture is an organic acid optionally containing halogen substituent.

10. The process as defined in claim 9, wherein as organic acid a $C_{1-3}$ organic acid is applied.

11. The process as defined in claim 1, wherein hexane:isopropanol:acetic acid mixture is applied as an eluent.

12. The process as defined in claim 5, wherein the aliphatic hydrocarbon is selected from the group consisting of pentane, hexane, heptane, octane, and cyclohexane.

13. The process as defined in claim 11, wherein the hexane:isopropanol:acetic acid mixture is in a ratio of (91-73%):(24-8.7%):(0.1-4.3%).

14. The process as defined in claim 1, wherein hexane:isopropanol:formic acid, hexane:isopropanol:trifluoro acetic acid, c-hexane:isopropanol:acetic acid, pentane:isopropanol:acetic acid, isooctane:isopropanol:acetic acid, hexane:dichloromethane:isopropanol, or diisopropyl ether:acetone:water is applied as an eluent.

15. The process as defined in claim 14, wherein the eluent is in a ratio of (91-73%):(24-8.7%):(0.1-4.3%).

16. The process as defined in claim 1, wherein the purified latanoprost acid of Formula IIa has a purity of 98.95-99.5%.

17. The process as defined in claim 1, further comprising preparing latanoprost from said latanoprost acid, wherein in the latanoprost thus obtained the isomeric impurities of trans-latanoprost and 15-epi-latanoprost are not individually more than 0.15%.

* * * * *